(12) United States Patent
Remkes et al.

(10) Patent No.: US 8,496,824 B2
(45) Date of Patent: Jul. 30, 2013

(54) METHOD AND DEVICE FOR SUPPLY OF A DIALYSIS UNIT WITH DIALYSIS FLUID

(75) Inventors: Gerard Remkes, Koblenz (DE); Gerhard Wiesen, Bad Hamburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1910 days.

(21) Appl. No.: 10/543,174

(22) PCT Filed: Jan. 14, 2004

(86) PCT No.: PCT/EP2004/000188
§ 371 (c)(1),
(2), (4) Date: Jul. 22, 2005

(87) PCT Pub. No.: WO2004/064886
PCT Pub. Date: Aug. 5, 2004

(65) Prior Publication Data
US 2006/0054215 A1   Mar. 16, 2006

(30) Foreign Application Priority Data
Jan. 24, 2003   (DE) .................... 103 02 691

(51) Int. Cl.
*B01D 63/00* (2006.01)
*C02F 1/44* (2006.01)

(52) U.S. Cl.
USPC ....... 210/321.71; 137/107; 210/85; 210/96.2; 210/138; 210/140; 210/143; 210/101; 210/195.2; 210/321.6; 210/636; 210/645; 210/646; 210/647; 210/739; 210/746

(58) Field of Classification Search
USPC .......................................... 137/107
See application file for complete search history.

(56) References Cited

U.S. PATENT DOCUMENTS

| | | | |
|---|---|---|---|
| 4,153,554 A | | 5/1979 | Von der Heide et al. |
| 4,386,634 A | * | 6/1983 | Stasz et al. ........... 141/2 |
| 4,895,657 A | | 1/1990 | Polaschegg |
| 5,744,027 A | | 4/1998 | Smejtek et al. |
| 2001/0040127 A1 | | 11/2001 | Donig et al. |
| 2002/0023880 A1 | * | 2/2002 | Pedrini et al. ........ 210/646 |

FOREIGN PATENT DOCUMENTS

WO    WO98/50091   * 11/1998   ................ 210/646

* cited by examiner

*Primary Examiner* — Dirk Bass
(74) *Attorney, Agent, or Firm* — Kenyon & Kenyon LLP

(57) ABSTRACT

A method and a device for supply of a dialyser in a dialysis unit with dialysis fluid is disclosed. At least one dialysis fluid concentrate is mixed with water to produce the dialysis fluid. The dialysis fluid concentrate is prepared in a reservoir unit in a given amount. A control and arithmetic unit calculates the dialysis fluid rate (Qd) such that, after a given treatment time ($T_B$) has passed, a given residual amount of dialysis fluid concentrate or no residual amount remains in the reservoir unit. It is preferable to empty the reservoir unit by the end of treatment.

11 Claims, 2 Drawing Sheets

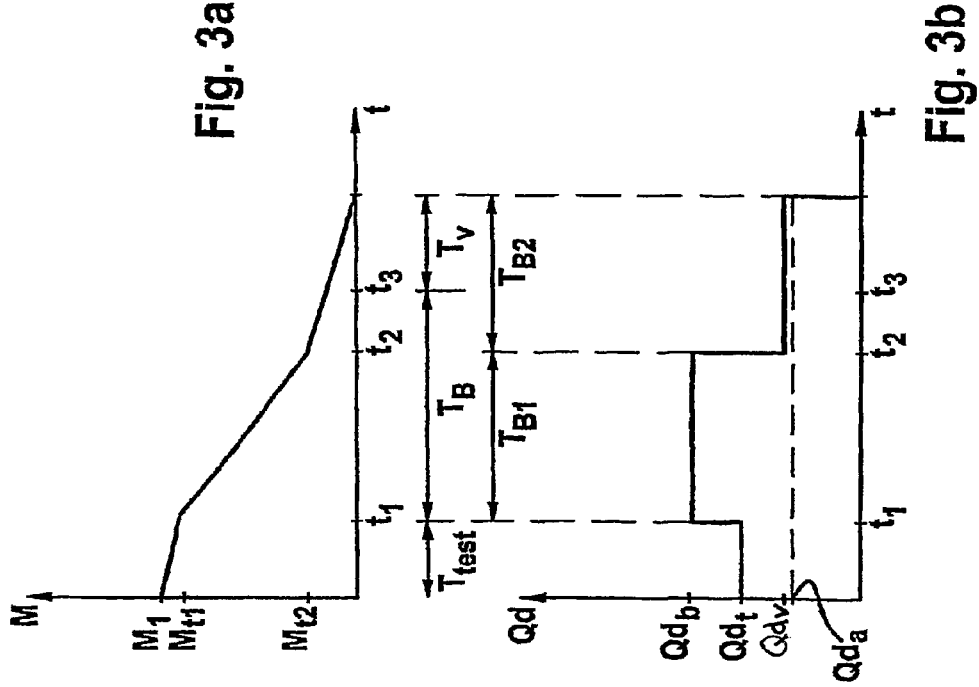
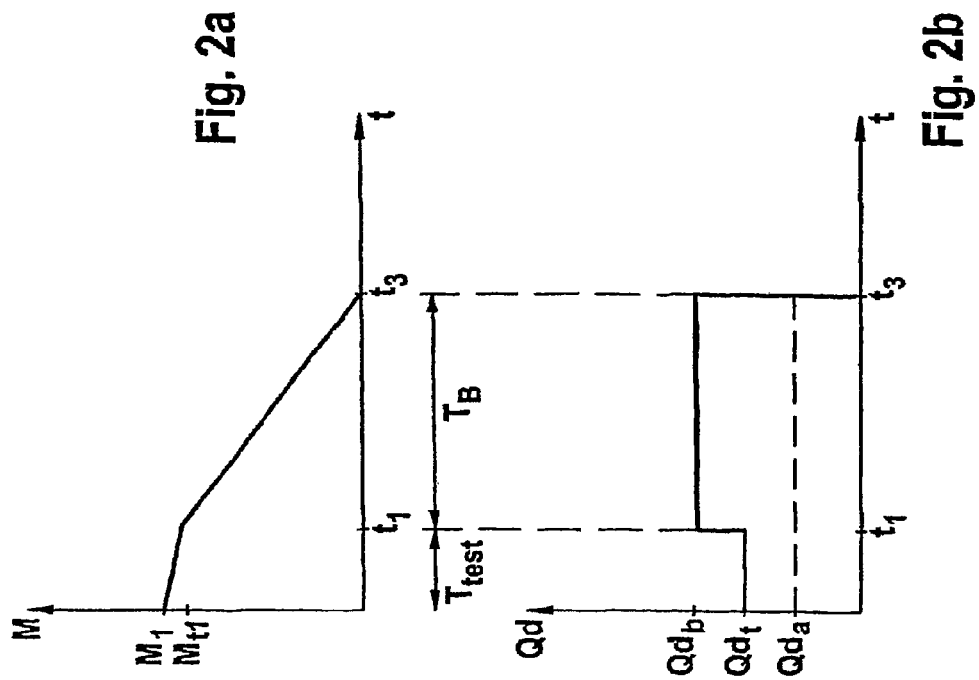

METHOD AND DEVICE FOR SUPPLY OF A DIALYSIS UNIT WITH DIALYSIS FLUID

FIELD OF THE INVENTION

The invention relates to a procedure and equipment for supplying a dialysis unit with dialysing fluid.

BACKGROUND OF THE INVENTION

It is customary today to use pre-prepared dialysing fluid concentrates to produce dialysing fluid for hemodialysis units, whereby the concentrate is diluted with water in the dialysis unit. In dialysis centers, dialysing fluid concentrates are made available either as pre-prepared products in canisters or bags or they are delivered via a ring piping system from a central tank.

The dialysing fluid is fed to the dialyser of the dialysis unit, which is divided by a semi-permeable membrane into a dialysing fluid chamber and a blood chamber. While the patient's blood flows continuously through the blood chamber, the dialysing fluid flows continuously as a counter-current through the dialysing fluid chamber.

Dialysing fluid concentrates supplied from a central source are easy to handle but have the disadvantage that they cannot be matched to the needs of an individual patient. Concentrates not provided from a central source permit adjustment of the dialysing fluid to suit individual patients but they must then be delivered to the dialysis unit in canisters or bags for each instance of dialysis treatment. In a normal situation it is necessary to use a canister with 5 or 6 liters of acid concentrate and a bag containing 650 to 750 g of sodium bicarbonate.

Since centrally-prepared concentrates can be drawn upon as necessary, no residual material arises, whereas pre-prepared concentrates intended for only a single treatment tend not to be used up. However, correct disposal of the packaging materials by granulation or combustion is only possible after the canister or bag has been completely emptied with the consequence that any residual material left in the canister or in the bag after treatment must be discarded. Furthermore, the disposal of the excess quantity of concentrate to waste constitutes a material loss.

A variety of types of equipment for the preparation of the dialysing fluid from concentrates and water is known. U.S. Pat. No. 4,895,657, for example, describes proportioning equipment in which two fluid concentrates are made available in concentrate containers, each fluid then being mixed and diluted with water in a pre-set ratio. Normally the concentrates are described as "35-fold", i.e. to a given volume of concentrate sufficient water is added so that the total volume is 35 times that of the concentrate. In practice this means that 1 part by volume of concentrate and 34 parts by volume of water are mixed together.

SUMMARY OF THE INVENTION

An object of the invention is to provide a procedure for supplying the dialyser of a dialysis unit with dialysing fluid which permits the dialysing fluid to be prepared in accordance with the specific need of the patient.

A further object of the invention is that of producing equipment permitting the provision of a dialysing fluid which is oriented towards the needs of individual patients.

In the case of the procedure or the equipment in accordance with the invention at least one dialysing fluid concentrate is made available in at least one receiving unit. Such receiving units may be, for example, containers, bags or the like.

The procedure or the equipment in accordance with the invention is based upon the principle that the rate of flow of the dialysing fluid during the dialysis treatment is so arranged that at the end of the treatment a pre-set residual amount of the dialysing fluid concentrate remains in the receiving unit or, alternatively, that the receiving unit is completely empty. In this context, the adjustment of the rate of flow of the dialysing fluid is related to the pre-set quantity of dialysing fluid concentrate at the commencement of the dialysis treatment, the pre-set volumetric ratio between the dialysing fluid concentrate and water and the pre-set duration of the treatment. The rate of flow of the dialysing fluid may remain constant during the treatment period or it may be varied.

The procedure or the equipment in accordance with the invention renders it possible to adjust the rate of flow of the dialysing fluid to a level which lies above the minimum rate necessary for the treatment so that the overall level of dialysance is increased.

In a conventional dialysis treatment, the doctor prescribes a particular dose level of dialysis by specifying appropriate rates of flow for the blood and the dialysing fluid for a particular type of dialyser as well as an appropriate treatment time. In practice, the quantities of concentrates made available are determined in such a manner that in general they are adequate for treatments with different dialysing fluid rates. Consequently, in practice the concentrate is not completely used up. The procedure or the equipment in accordance with the invention makes use of the residual amount of concentrate to permit a higher rate of flow of the dialysing fluid. This has the advantage that when a higher rate of flow is used, the dialysing dose rate is increased which has a beneficial effect upon the treatment. For example, the efficiency of a hollow fiber dialyser increases with increasing rates of flow of dialysing fluids up to an asymptotic limiting value.

For the reasons identified above, in principle an effort is made to ensure that the dialysing fluid in the receiving unit is used up by the end of the treatment. In practice, however, it can be useful in individual instances to control the rate of flow of the dialysing fluid in such a manner that a pre-set residual volume of dialysing fluid concentrate should still remain in the receiving unit to provide a reserve. For example, such a reserve may be necessary if the treatment is interrupted once or more often because of complications and when for the period of the interruption the dialysing fluid flows to waste.

The pre-set residual quantity of concentrate can then be used to prepare the dialysing fluid in a quantity necessary for an appropriate extension of the treatment, thus ensuring that the effective length of treatment is attained.

Preferably, the pre-set residual volume of dialysing fluid is discharged to waste at the end of the treatment so that the receiving unit is completely empty. Preferably, the pre-set residual dialysing fluid is diluted with water in a pre-set volumetric ratio to ensure that the diluted concentrate may be discharged to waste without causing any problems.

The pre-set volume of dialysing fluid concentrate, the pre-set volumetric ratio and the pre-set treatment time can be entered manually or they may be scanned in automatically. For example, the data may be recorded in the form of a bar code on the containers or bags and read off by means of a reading device.

In a preferred embodiment of the procedure or the equipment in accordance with the invention, the flow rate of the dialysing fluid over the full duration of the treatment is determined before the commencement of the dialysis treatment from the pre-set quantity of dialysing fluid concentrate at the beginning of the treatment, the pre-set volumetric ratio of the concentrate and water and the pre-set treatment time. The rate of flow of the dialysing fluid can then be set for the total period of the treatment time in such a manner that there remains in the receiving unit either no concentrate or the pre-set residual volume.

An alternative embodiment provides for the initial setting of a pre-set dialysing fluid flow rate for a pre-set time interval which should form a substantial part of the overall dialysis treatment, the dialysing fluid flow rate which is to be set for the remaining treatment time being determined only at the end of the pre-set time interval such that at the end of the treatment the receiving unit contains either no residual dialysing fluid concentrate or the pre-set residual volume. To achieve this, following the end of the pre-set time interval determination is made of the flow rate based on the remaining dialysing fluid concentrate in the receiving unit, the pre-set volumetric ratio and the remaining treatment time. The amount of dialysing fluid concentrate in the receiving unit is determined from the pre-set volume of concentrate at the beginning of the dialysis treatment and the amount of dialysing fluid concentrate used. If the proportioning activity is performed by a pump providing a constant relationship between the number of operating cycles, i.e. piston strokes, revolutions or the like and the volume conveyed, the quantity of dialysing fluid concentrate used can be calculated in a simple manner regardless of any external operating conditions. In the event of one or more interruptions to the dialysis treatment during the pre-set time interval the treatment time can be lengthened by a corresponding amount and then the optimal flow rate of dialysing fluid can be determined on the basis of the increase in treatment time.

If several concentrates in several receiving units are employed, a residual amount can only be pre-set for one of the receiving units if the receiving units have different capacities and the volumetric ratios of concentrate and water are different. In that situation, the calculation of the flow rate of the dialysing fluid should then be made on the basis of the pre-set volume of concentrate in the receiving unit which is the first to be fully used.

Various types of dialysis equipment provide for a test to be carried out over a pre-set time interval before the dialysis treatment commences. To determine the pre-set amount of dialysing fluid concentrate at the commencement of the dialysis treatment a calculation is made using the quantity of dialysing fluid concentrate in the receiving unit before the test and the quantity of dialysing fluid concentrate used during the pre-set time interval in order to determine the quantity of concentrate in the receiving unit before commencement of the dialysis treatment.

BRIEF DESCRIPTION OF THE DRAWINGS

FIGS. 2a and 2b show the volume of concentrate or the rate of flow of the dialysing fluid as a function of time for a first exemplary embodiment of the invention.

FIGS. 3a and 3b show the volume of concentrate or the rate of flow of the dialysing fluid as a function of time for a second exemplary embodiment of the invention.

DETAILED DESCRIPTION

Figure 1:
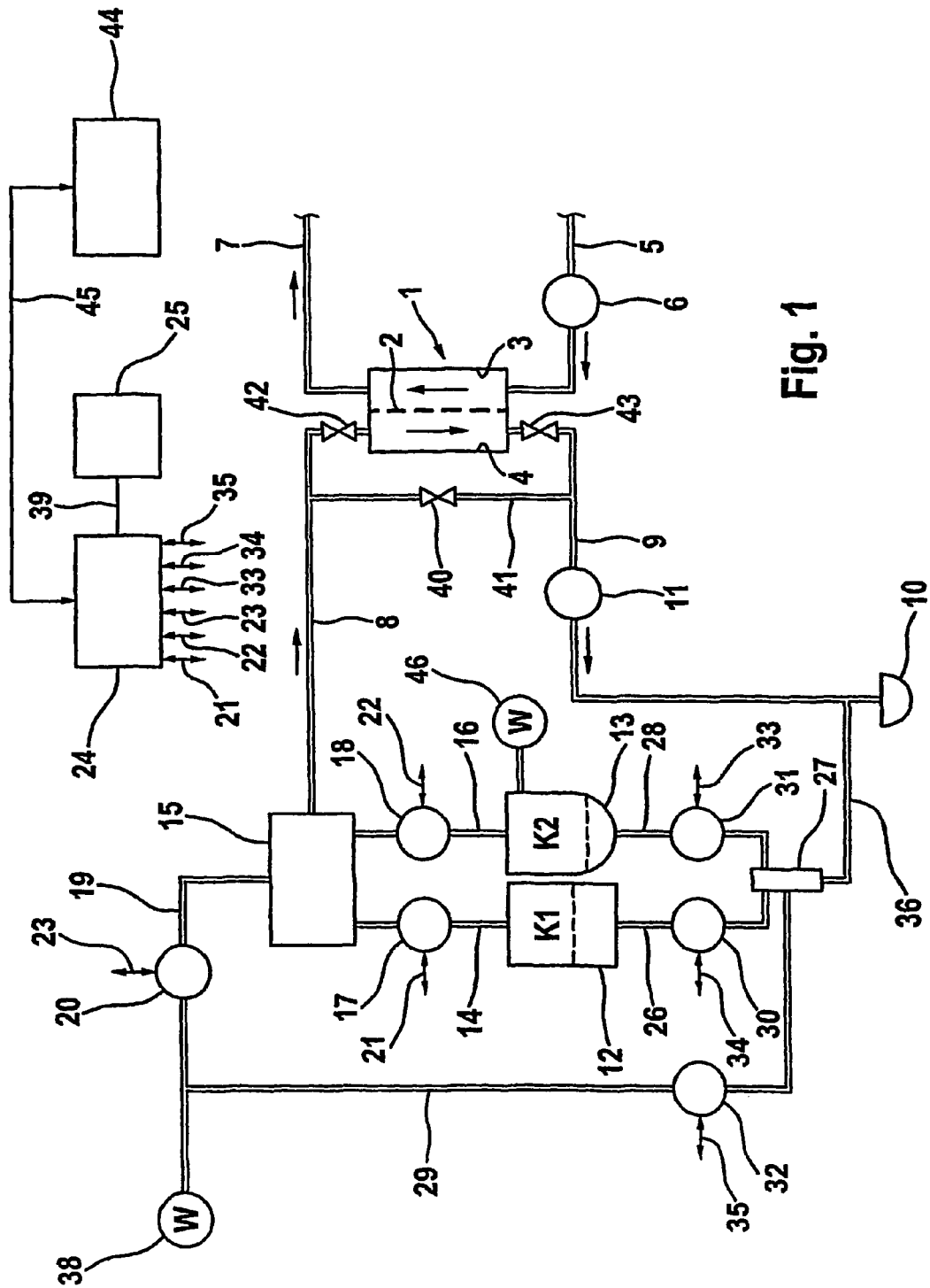
FIG. 1 is a very simplified schematic representation of equipment for supplying a dialyser of a dialysis unit together with the dialysing equipment.

In the following, two embodiment examples of the procedure and the equipment in accordance with the invention are explained in more detail by reference to the drawings.

The hemodialysis equipment exhibits a dialyser 1 which is divided into a blood chamber 3 and a dialysing fluid chamber 4 by a semi-permeable membrane 2. The inlet to the blood chamber 3 is connected to one end of blood supply pipe 5 in line with a blood pump 6 while the outlet of the blood chamber is connected to the end of a blood return pipe 7. A dialysing fluid supply pipe 8 leads to the inlet of the dialysing fluid chamber 4 and from the outlet of the dialysing fluid chamber a dialysing fluid outflow pipe 9 leads to a waste discharge 10. A dialysing fluid pump 11 is in line with the dialysing fluid outflow pipe 9. During the course of the dialysis treatment, the patient's blood flows through the blood chamber 3 of the dialyser 1 while a counterflow of dialysing fluid passes through the dialysing fluid chamber 4.

In general, the equipment for supplying the dialyser with dialysing fluid is a component part of the dialysis unit. In principle, however, the supply equipment may also be a separate unit. There follows a detailed description of the supply equipment.

To prepare the dialysing fluid, two concentrates K1 and K2 are mixed with water in a pre-set ratio by volume. Examples of the directions given for this dilution consist of a "35-fold" or "45-fold" ratio, i.e. one part by volume of the concentrate is mixed with 34 or 44 parts by volume of water. When a dry concentrate in powder form is used instead of a fluid concentrate the weight of the powder is first converted to an equivalent volume of fluid concentrate in order that the concentrate may be mixed with water in accordance with the pre-set volumetric ratio.

The supply equipment contains two receiving units for the two concentrates; one of these is a canister 12 which is filled with 5 or 6 liters of acid concentrate and the other is a bag 13 which is filled with 650 to 750 g of sodium bicarbonate.

A first concentrate pipe 14 connects the canister 12 with mixing chamber 15 and a second concentrate pipe 16 connects the bag 13 to the mixing chamber 15. Proportioning pumps 17 and 18 are connected into respectively the first and second concentrate pipes 14 and 16. Furthermore, a water supply pipe 19 connected to a source of water 38 feeds into the mixing chamber 15. A proportioning pump 20 is also connected into the water supply pipe 19.

The proportioning pumps 17, 18 and 20 are connected by data and control leads 21, 22 and 23 to a central control and calculating unit 24, which instructs the proportioning pumps to operate at particular rates of flow so that the concentrates and water are mixed in a pre-set volume ratio to produce the dialysing fluid in the mixing chamber 15. The bag 13 containing the dry concentrate possesses a water inlet 46 through which a specified volume of water passes. In order to obtain a fluid concentrate from the dry concentrate—by mixing with water in a pre-set volumetric ratio—the powder is first dissolved in water which enters the bag via the water inlet.

In addition, the supply equipment possesses an input unit 25 which communicates with the central control and calculating unit 24 by a data lead 39.

An emptying pipe 26 runs from the canister 12 and connects with a second mixing chamber 27 while a second emptying pipe 28 runs from the bag 13 and is connected to the mixing chamber 27. A water pipe 29 connects the source of water with the mixing chamber 27. In the first and second emptying pipes 26 and 28 and in the water pipe 29 there are respectively integrated pumps 30, 31 and 32 which are connected via control leads 33, 34 and 35 with the central control and calculating unit 24. A waste discharge pipe 36 runs from the mixing chamber 27 to the waste discharge outlet 10.

To facilitate an interruption of the dialysis treatment, for example if complications develop or if it is necessary to carry out a test the unit is fitted with a by-pass pipe 41 with a by-pass valve 40 together with an up-stream stop-valve 42 and a down-stream stop valve 43 with respect to the dialysing fluid chamber 4 of the dialyser 1. If the dialysis treatment is interrupted, the dialysing fluid flows through the by-pass pipe 41 into the waste discharge pipe 10 which means that there is no flow of dialysing fluid through the dialysing fluid chamber 4.

The hemodialysis unit is also provided with a central control and calculating unit 44, which communicates by a data lead 45 with the control and calculating unit 24 of the supply equipment.

There now follows a detailed description of the method of functioning of the supply equipment.

In a first embodiment, the control and calculating unit 24 of the supply equipment controls the operation of the pumps in such a manner that the following process steps are carried out.

Before the dialysis treatment commences, the quantities $M_1$ and $M_2$ of fluid concentrate within the canister 12 and the bag 13, respectively, are entered into the data input unit 25. Furthermore, the data relating to the effective treatment time Tb together with the volumetric ratio $V_1$, $V_2$ of concentrate K1 or K2, respectively, and water W are also entered into the data input unit 25.

To prepare the dialysing fluid which is to be fed to the dialyser 1, the control and calculating unit 24 sets the flow rates of the proportioning pumps 17, 18 and 20 such that the concentrates K1 and K2 are each mixed in the mixing chamber with water in the pre-set volumetric ratio.

During the course of an initial test and preparation phase the control and calculation unit 44 of the dialysis unit closes the stop valves 42, 43 and opens the by-pass valve 40 so that the dialysing fluid flows through the by-pass pipe 41 to the waste outlet 10 for a pre-set time interval $T_{test}$. The flow rate of dialysing fluid amounts, for example, to $Qd_r$. At the end of the time interval $T_{test}$ the effective dialysis treatment commences.

The control and calculation unit 24 now calculates the quantity of concentrate which was used during the time interval $T_{test}$ from the pre-set rates of flow of the proportioning pumps 17 and 18. From the differences between the pre-set concentrate quantities M1, M2 and the amount of concentrate used during the time interval $T_{test}$ the control and calculation unit 24 now determines the quantity of concentrate remaining in the container 12 or the bag 13 at the time the effective dialysis treatment commences.

The attempt should be made during the course of the dialysis treatment to ensure that, if at all possible, both receiving units should be completely emptied. In practice, however, this is not possible if the contents of the canister 12 and the bag 13 are not in the precise desired relationship to one another. Therefore, the control and calculating unit selects the receiving unit which is to be completely emptied. In the present exemplary embodiment, it is assumed that it is the canister 12 which is to be emptied completely. In principle, of course, it can also be decided that a pre-set residual volume should be retained in the canister 12. The cited decisions are, of course, only given by way of example. Thus, the control and calculation unit 24 can prescribe which receiving unit is to be emptied completely in such a manner that the smallest possible residual quantity should be left in the other receiving unit.

The control and calculating unit 24 now calculates the dialysis flow rate $Q_d$ which is required to ensure that there is no residual volume of concentrate in the canister at the end of the treatment time; to do this it uses the quantity $M_{r1}$ of the concentrate remaining in the canister 12 at the beginning of the effective dialysis treatment after the test at time point $t_1$, the pre-set duration of the treatment $T_B$ and the pre-set volumetric relationship $V_1$ of the acid concentrate K1 and water W. The instruction for this rate of flow of the dialysing fluid is transmitted via the data lead 45 to the control and calculation unit 44 of the dialysis unit, which then sets the corresponding supply rate of the dialysing fluid pump 11.

FIGS. 2a and 2b show the volume M of the concentrate in the canister 12 and the flow rate of the dialysing fluid Qd as a function of the time t. It can clearly be seen that a first constant flow rate of dialysing fluid $Qd_t$ has been set for the test at time point 0 and that a second constant flow rate $Qd_b$ has been set for the effective dialysis treatment at time point $t_1$ this having been calculated to ensure that at the end of the dialysis treatment at time point $t_3$ all the concentrate has been consumed.

Although the canister 12 is completely empty a residual volume of concentrate is left in bag 13. To empty the bag, the control and calculating unit 24 actuates the proportioning pumps 31 and 32 to draw off the concentrate remaining in bag 13. The concentrate is mixed with water in the mixing chamber 27 with the pump 32 supplying this water in the required ratio by volume. The diluted concentrate then flows to the waste discharge 10 through the waste pipe 36. Finally, both the canister and the bag can be removed from the unit and disposed of in a suitable manner.

In the event that a complication develops during the effective dialysis treatment, the dialyser 1 is disconnected and the dialysing fluid flows to waste via the by-pass 41. If frequent interruptions occur it can be necessary to prolong the dialysis treatment by an appropriate time in order to attain the desired effective treatment time of $T_{eff}$. However, in the above exemplary embodiment this is not possible because by the end of the treatment at time point $t_3$ no further quantity of concentrate is available.

FIG. 2b displays the bloodflow $Qd_a$ which the doctor would prescribe in the case of a conventional dialysis treatment in order to provide a particular dialysis dosing rate. It is seen clearly that the bloodflow with the procedure in accordance with the invention is greater than the rate of $Qd_a$ which would be set by the doctor with the consequence that the dialysis dosing rate has been increased.

There follows a description of a second exemplary embodiment which permits the treatment to be lengthened in the event of one or several interruptions. The second exemplary embodiment differs from the first example only in that the control and calculating unit 24 of the supply equipment lays down a different program sequence.

Firstly, a test is carried out as in the case of the first exemplary embodiment. When the test has been completed and some dialysing fluid has been disposed of to waste the control and calculating unit 24 determines once again the quantity of concentrate present in the canister 12 or the bag 13 at the beginning of the dialysis treatment (time point $t_1$) and decides which container is the one to be completely emptied. It is again assumed that there will be no residual concentrate left in canister 12.

Then the control and calculating unit 24 determines a dialysing fluid flow rate Qd for a pre-set time interval $T_{B1}$ which should constitute the essential part of the treatment, the rate being equal to the rate calculated in the first exemplary embodiment. In principle, however, the flow rate may be greater or less. Nevertheless it should be of such a value that after the end of the time interval $T_{B1}$ ending at $t_2$, canister 12 still contains a sufficient volume of concentrate to permit the treatment to be extended beyond the pre-set time $T_B$.

After the end of the time interval $T_{B1}$ the control and calculating unit 24 of the dialysis unit determines the time period $T_v$ of the interruption of the dialysis treatment. This is the extra time by which the treatment should be continued beyond the pre-set treatment time $T_B$.

The control and calculating unit 24 of the supply equipment now calculates the remaining treatment time $T_{B2}$ from the pre-set treatment time $T_B$, the pre-set time interval $T_{B1}$ and the time period $T_v$ by which the treatment time should be extended.

Then the control and calculating unit 24 calculates the volume $M_{t2}$ of concentrate still held in canister 12 at time point $t_2$ from the volume of concentrate $M_1$ fed into the data input unit 25, i.e. the pre-set volume of concentrate and the volume of concentrate which was used during the test and the pre-set time interval $T_{B1}$.

From the remaining treatment time $T_{B2}$ and the volume of concentrate $M_{t2}$ remaining in canister 12, the control and calculating unit 24 then calculates the flow rate $Qd_v$ which is to be set in order that the canister 12 is completely empty at the end of the treatment. This dialysing fluid flow rate is then set for the remaining treatment.

FIGS. 3a and 3b also show the volume of concentrate in canister 12 and the dialysing fluid flow rate Qd as a function of the time t. It can be seen clearly that the treatment will be given over a pre-set time interval $T_{B1}$, at first at a dialysing fluid flow rate of $Qd_{b1}$ which is the same as in the first embodiment example and that after a time interval of $T_{B1}$ a lower dialysing fluid flow rate $Qd_v$ applies, this being calculated so as to ensure that canister 12 is completely empty at the end of the treatment.

Furthermore, it is clear that the blood flow rate with the procedure in accordance with the invention is greater than blood flow rate $Qd_a$ which the doctor would specify in the case of conventional treatment.

At the end of the treatment the residual volume of concentrate in the bag 13 is again diluted with water and allowed to flow to waste with the result that both the canister and the bag can be removed and disposed of.

To dispose of the residual volume of concentrate, in principle it is not necessary to use the pipes 26, 28, 29 and 36 and the relevant pumps 30, 31 and 32 and the mixing chamber 27. In an alternative embodiment the control and calculating unit 44 switches the hemodialysis unit to a condition where the residual volume of concentrate is disposed of via the "by-pass", i.e. the valves 42 and 43 are closed and the valve 40 is opened until the residual volume has been drained to waste. This embodiment has the advantage that neither an additional mixing chamber or additional piping and pumps are necessary. Consequently, this embodiment might be preferred in practice.

It should be noted that the supply equipment in accordance with the invention permits the most widely different dialysing fluid flow rates to be pre-set. The only decisive requirement is that the dialysing fluid flow rate be set so as to be compatible with the volume of concentrate, the volumetric ratio and the treatment time.

The invention claimed is:

1. An apparatus for supplying a dialyser of a dialysis unit with a dialysing fluid, the apparatus comprising:
   at least one receiving unit for receiving only at least one dialysing fluid concentrate;
   means for providing water for a dilution of the at least one dialysing fluid concentrate;
   means for mixing the at least one dialysing fluid concentrate and the water in a first pre-set volumetric ratio to prepare the dialysing fluid, said means for mixing connected to the at least one receiving unit and configured to receive the at least one dialysing fluid concentrate therefrom;
   a means for setting a dialysing fluid flow rate $Qd_b$ during a dialysis treatment such that at the end of the pre-set treatment period $T_B$, the at least one receiving unit is either empty or contains a pre-set residual volume of the at least one dialysing fluid concentrate;
   wherein the dialysing fluid flow rate $Qd_b$ is dependent upon a pre-set volume of the at least one dialysing fluid concentrate at a commencement of a dialysis treatment period, the first pre-set volumetric ratio, and the pre-set treatment period $T_B$.

2. The apparatus of claim 1, wherein the means for setting a dialysing fluid flow rate $Qd_b$ determines the dialysis fluid flow rate $Qd_b$ before the commencement of the dialysis treatment period from the pre-set volume of the at least one dialysing fluid concentrate at the commencement of the dialysis treatment period, the first pre-set volumetric ratio, and the pre-set treatment period $T_B$,
   wherein the means for setting is configured to set the dialysing fluid flow rate $Qd_b$ over the pre-set treatment period $T_B$ such that at the end of the pre-set treatment period $T_B$, the at least one receiving unit is either empty or contains the pre-set residual volume of the at least one dialysing fluid concentrate.

3. The apparatus of claim 1, further comprising:
   a means for testing the apparatus over a pre-set time interval $T_{test}$ before the commencement of the dialysis treatment period, and
   a means for determining a volume of the at least one dialysing fluid concentrate in the at least one receiving unit from the pre-set volume of the at least one dialysing fluid concentrate at the commencement of the dialysis treatment period and a volume of the at least one dialysing fluid concentrate used during the pre-set time interval $T_{test}$.

4. An apparatus for supplying a dialyser of a dialysis unit with a dialysing fluid, wherein a dialysis treatment period equals a pre-set time interval $T_{B1}$ plus a remaining dialysis treatment period $T_{B2}$, the apparatus comprising:
   at least one receiving unit for receiving only at least one dialysing fluid concentrate;
   means for providing water for a dilution of the at least one dialysing fluid concentrate;
   means for mixing the at least one dialysing fluid concentrate and the water in a first pre-set volumetric ratio to prepare the dialysing fluid, said means for mixing connected to the at least one receiving unit and configured to receive the at least one dialysing fluid concentrate therefrom;
   a means for supplying the dialysing fluid to the dialyser at a pre-set dialysing fluid flow rate $Qd_{b1}$ over the pre-set time interval $T_{B1}$ such that an amount of the at least one dialysing fluid concentrate remaining in the at least one receiving unit at the end of the pre-set time interval $T_{B1}$ can be determined from the pre-set volume of the at least one dialysing fluid concentrate at the commencement of the dialysis treatment period and an amount of the at least one dialysing fluid concentrate used up during the dialysis treatment period, and
   a means for setting a dialysing fluid flow rate $Qd_v$ over the remaining dialysis treatment period $T_{B2}$ which depends upon a volume of the at least one dialysing fluid concentrate in the at least one receiving unit at the end of the pre-set time interval of the dialysis treatment $T_{B1}$, the first pre-set volumetric ratio, and the remaining dialysis treatment period $T_{B2}$, such that at the end of the dialysis treatment period, the at least one receiving unit is either empty or contains the pre-set residual volume of the at least one dialysing fluid concentrate.

5. The apparatus of claim 2, further comprising:
means for discharging the pre-set residual volume of the at least one dialysing fluid concentrate to waste via a waste discharge outlet;
wherein at the end of the pre-set treatment period $T_B$ the at least one receiving unit contains the pre-set residual volume of the at least one dialysing fluid concentrate, and the pre-set residual volume is capable of being discharged to the waste discharge outlet.

6. The apparatus of claim 5, further comprising:
means for mixing the pre-set residual volume of the at least one dialysing fluid concentrate with water in a second pre-set volumetric ratio;
wherein the pre-set residual volume is capable of being diluted with water before the pre-set residual volume is discharged to the waste discharge outlet.

7. The apparatus of claim 2, wherein at the end of the pre-set treatment period $T_B$, the at least one receiving unit is empty.

8. The apparatus of claim 1, further comprising:
means for inputting data relevant to the pre-set volume of the at least one dialysing fluid concentrate at the commencement of a dialysis treatment period, the first pre-set volumetric ratio, and the pre-set treatment period.

9. The apparatus of claim 1, wherein the at least one receiving unit comprises two receiving units.

10. The apparatus of claim 4, further comprising:
means for discharging the pre-set residual volume of the at least one dialysing fluid concentrate to waste via a waste discharge outlet;
wherein at the end of the remaining dialysis treatment period $T_{B2}$ the at least one receiving unit contains the pre-set residual volume of the at least one dialysing fluid concentrate, and the pre-set residual volume is capable of being discharged to the waste discharge outlet.

11. The apparatus of claim 4, wherein at the end of the remaining dialysis treatment period $T_{B2}$, the at least one receiving unit is empty.

* * * * *

UNITED STATES PATENT AND TRADEMARK OFFICE
CERTIFICATE OF CORRECTION

PATENT NO. : 8,496,824 B2 Page 1 of 1
APPLICATION NO. : 10/543174
DATED : July 30, 2013
INVENTOR(S) : Remkes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1842 days.

Signed and Sealed this
Fifteenth Day of September, 2015

Michelle K. Lee
*Director of the United States Patent and Trademark Office*